US006180602B1

(12) United States Patent
Kato et al.

(10) Patent No.: US 6,180,602 B1
(45) Date of Patent: Jan. 30, 2001

(54) HUMAN NOVEL CDNA, TGF-BETA SUPERFAMILY PROTEIN ENCODED THEREBY AND THE USE OF IMMUNOSUPPRESSIVE AGENT

(75) Inventors: Seishi Kato, Sagamihara; Suwan Oh, Taejion; Shingo Sekine; Mihoro Saeki, both of Sagamihara; Midori Kobayashi, Fujisawa; Mika Yada, Sagamihara; Tomoko Tsuji, Yokohama; Hitoshi Ohmori, Okayama, all of (JP)

(73) Assignee: Sagami Chemical Research Center, Tokyo (JP)

( * ) Notice: Under 35 U.S.C. 154(b), the term of this patent shall be extended for 0 days.

(21) Appl. No.: 08/775,882

(22) Filed: Jan. 2, 1997

Related U.S. Application Data

(63) Continuation-in-part of application No. 08/390,207, filed on Feb. 16, 1995, now Pat. No. 6,051,424, which is a continuation-in-part of application No. 08/379,441, filed on Feb. 3, 1995, now abandoned.

(30) Foreign Application Priority Data

Aug. 4, 1992 (JP) .................................................. 4-208077
Nov. 13, 1992 (JP) .................................................. 4-327619
Feb. 26, 1993 (JP) .................................................. 5-61431

(51) Int. Cl.$^7$ .......................... A61K 38/18; C07K 14/495
(52) U.S. Cl. ........................... 514/12; 530/300; 530/350; 530/868
(58) Field of Search ........................... 514/12; 530/350, 530/300, 868

(56) References Cited

U.S. PATENT DOCUMENTS

| 4,727,138 | 2/1988 | Goeddel et al. ........................ 536/27 |
| 4,762,791 | 8/1988 | Goeddel et al. ..................... 435/243 |
| 4,925,793 | 5/1990 | Goeddel et al. ................... 435/69.51 |
| 4,929,554 | 5/1990 | Goeddel et al. ................... 435/172.3 |
| 5,008,240 | * 4/1991 | Bentz et al. ............................ 514/2 |
| 5,096,705 | 3/1992 | Goeddel et al. ..................... 424/85.5 |
| 5,189,189 | 2/1993 | Misawa et al. ....................... 554/194 |
| 5,246,841 | 9/1993 | Yazawa et al. ...................... 435/134 |

FOREIGN PATENT DOCUMENTS

| 594 868 | 5/1994 | (EP) . |
| 1-35639 | 7/1989 | (JP) . |
| 4-117292 | 4/1992 | (JP) . |
| 93/23545 | 11/1993 | (WO) . |
| WO 97/00958 | 9/1997 | (WO) . |

OTHER PUBLICATIONS

Massagué J. The transforming growth factor–beta family. Ann. Rev. Cell Biol., (1990) 6 597–641.*
Creighton TE. (1984) Proteins: Structures and Molecular Properties. W.H. Freeman, New York, 1984.*
Okubo et al. GenBank Accession No. D11716. Dec. 1, 1992.
Okubo et al. GenBank Accession No. D11717. Dec. 1, 1992.
Dakour et al. GenBank Accession No. U51731. Oct. 2, 1996.
Johns et al., Lipids of the Marine Bacterium Flexibacter polymorphus, Arch. Microbiol., 1977, vol. 114, pp. 267–271.
DeLong et al., Biochemical Function and Ecological Significance of Novel Bacterial Lipids in Deep–Sea Procaryotes, App. Environ. Microbiol., 1986, vol. 51, No. 4, pp. 730–737.
Wirsen et al., Membane Lipids of a Psychrophilic and Barophilic Deep–Sea Bacterium, Curr. Microbiol., 1987, vol. 14, pp. 319–322.
Yazawa et al., Production of Eicosapentaenoic Acid by Marine Bacteria, J. Biochem., 1988, vol. 103, pp. 5–7.
Yazawa et al., Eicosapentaenoic Acid Productivity of the Bacteria Isolated from Fish Intestines, Nippon Suisan Gakkaishi, 1988, vol. 54, No. 10, pp. 1835–1838.
Nichols et al., Anaerobic Production of Polyunsaturated Fatty Acids by *Shewanella putrefaciens* Strain ACAM 342, FEMS Microbiol. Lett., 1992, vol. 98, pp. 117–122.
Ringø et al., Production of Eicosapentaenoic Acid (20:5 n–3) by *Vibrio pelagius* Isolated from Turbot Larvae, App. Environ. Microbiol, 1992, vol. 58, No. 11, pp. 3777–3778.
Ringø Production of Eicosapentaenoic Acid by Freshwater Vibrio, Lipids, 1992, vol. 27, No. 7, pp. 564–566.
Shimizu et al., *Fungal Mycelia* as a Novel Source of Eicosapentaenoic Acid, Biochem. Biophys. Res. Commun., 1988, vol. 150, No. 1, pp. 335–341.
Shimizu et al., Production of Eicosapentaenoic Acid by *Mortierella Fungi*, Jour. Amer. Oil Chem. Soc., 1988, vol. 65, No. 9, pp. 1455–1459.
Nielsen et al., "The Mouse Protein Synthesis Initiation Factor 4A Gene Family Includes Two Related Functional Genes Which are Differentially Expressed", The EMBO Journal, vol. 7, No. 7, 1988, pp. 2097–2105.
Huhtala et al., "Complete Structure of the Human Gene for 92–kDa Type IV Collagenase", The Journal of Biological Chemistry, vol. 266, No. 25, Sep. 5, 1991, pp. 16485–16490.
Adams et al., "Sequence Identification of 2,375 Human Brain Genes", Nature, vol. 355, Feb. 13, 1992, pp. 632–634.
Bowie et al. Deciphering the message in protein sequences: tolerance to amino acid substitutions. Science, (Mar. 16, 1990) 247 (4948) 1306–10.*
Ngo et al., in The Protein Folding Problem and Tertiary Structure Prediction, Merz and Le Grand (Eds), Aug. 1994, Springer Verlag, pp. 433 and 492–495, Mar. 1990.*
Lodish et al. Molecular Cell Biology, 3rd edition, Mar. 1995, W. H. Freeman & Co., p. 266.*

* cited by examiner

*Primary Examiner*—David S. Romeo
(74) *Attorney, Agent, or Firm*—Foley & Lardner

(57) ABSTRACT

Isolated cDNAs derived from mRNAs expressed in human cells are provided, as are DNAs and RNAs comprising their nucleotide sequences, and vectors for expressing the cDNAs. The cDNAs encode proteins which have functions similar to known proteins.

7 Claims, 4 Drawing Sheets

FIGURE 4

```
HP: (Residues 211-308 of SEQ ID NO: 6)  CRLHTVRASL-EDLGWADWVLSPREVQVTMGIGAC--P-----SQFRAANMH-AQIKTSLHRLKPDTVPAPCCVPASYNPM-VLIQKTDTGVSLQTYDDLLAKDCHCI BM: (SEQ ID NO: 7)                      ..K.ELYV.F-Q....Q..IIA.KGYAANY.D.E.SF.--L--NAHMN.TN..-.IVQ.LV.LMN.EY..K...A.TKL.AIS..YFDDNSN.I.KK.RNMVVRA.G.H GD: (SEQ ID NO: 8)                      ..ARRLYV.F-REV..HR..IA..GFLANY.Q.Q.AL.VALSG.GGPP.LN.--.VLRALM.AAA.GAADL......RLS.IS..FFDNSDN.V.RQ.E.MVVDE.G.R IN: (SEQ ID NO: 9)                      ...QQFFIDF-RLI..N..IIA.TGYYGNY.E.S.--.AYLAGVPGSASSF.T.VVNQYRM.GLNPGTVNS..I.TKLST.SM.YFDDEYNIVKRDVPNMIVEE.G.A TG: (SEQ ID NO: 10)                     .-.RPLYIDFKR....K-.IHE.KGYNANF.A...--.-.YL----WSSDTQ.SRVL-SLYNTIN.EASAS....SQDLEPLTI.YYIGK.PKIE.-LSNMIV.S.K.S

*        **   *            *        *                                                 
```

HUMAN NOVEL CDNA, TGF-BETA SUPERFAMILY PROTEIN ENCODED THEREBY AND THE USE OF IMMUNOSUPPRESSIVE AGENT

CROSS REFERENCE TO RELATED APPLICATION

This application is a continuation-in part application of Ser. No. 08/390,207, U.S. Pat. No. 6,051,424, filed on Feb. 16, 1995, which was a continuation-in-part application of Ser. No. 08/379,441, abandoned, filed on Feb. 3,1995, now abandoned.

TECHNICAL FIELD

The present invention relates to human cDNA derived from mRNA expressed in human cells, TGF-beta superfamily protein encoded thereby, the vectors containing the cDNA, and a process for utilizing such proteins or DNA for therapeutic purpose as immunosuppressive agents. The human cDNA of the present invention can be used as a probe for gene diagnosis and as gene resources for mass production of the protein encoded thereby. The protein of the present invention can be used as medicine such as a therapeutic agent for autoimmune diseases, or as an antigen for preparing the antibodies against the protein. The cDNA vector of the invention facilitates preparation of probes and expression of the protein.

BACKGROUND ART

Human cells produce many secretory proteins involved in cell growth and cell differentiation. TGF-beta superfamily proteins, which belong to the secretory proteins, have attracted a great deal of attention as a potential therapeutic agent because of their diverse biological activities [Massague, J., Annu. Rev. Cell Biol. 6: 597–641, 1988]. For example, TGF-beta 2, activin, inhibin, and bone morphogenetic proteins (BMP) are known as members of TGF-beta superfamily showing various biological activities including promotion and inhibition of cell growth, promotion and inhibition of cell differentiation, as well as promotion and inhibition of other cell functions. Thus these proteins have been investigated for using as medicine such as therapeutic agents for wound-healing, bone-related disease, anti-inflammation, and autoimmune diseases.

The carboxyl terminal of about 100 to 140 amino acid residues in TGF-beta superfamily proteins contains a characteristic amino acid sequence in which the position of seven cysteines is conserved. It is expected that there are many novel TGF-beta superfamily proteins playing an important role in a living cell.

Immunosuppressive agents such as steroid, cyclosporin, and FK506 have been used for therapy of autoimmune diseases or during an organ transplantation. However these compounds cause side effects, so that a new type of immunosuppressive agent has been desired.

DISCLOSURE OF INVENTION

It is therefore an object of the present invention to provide a human novel cDNA encoding TGF-beta superfamily protein, the protein encoded thereby, and a process for utilizing such proteins or DNA for therapeutic purpose as immunosuppressive agents.

BRIEF DESCRIPTION OF THE DRAWINGS

FIG. 4 shows the alignment of the C terminal 98 amino acid residues of the deduced sequence HP of the novel human TGF-beta superfamily protein according to the invention with human BMP-6 (BM), GDF-1 (GD), inhibin beta (IN), and TGF beta 2 (TG).

BEST MODE FOR CARRYING OUT THE INVENTION

Figure 1:
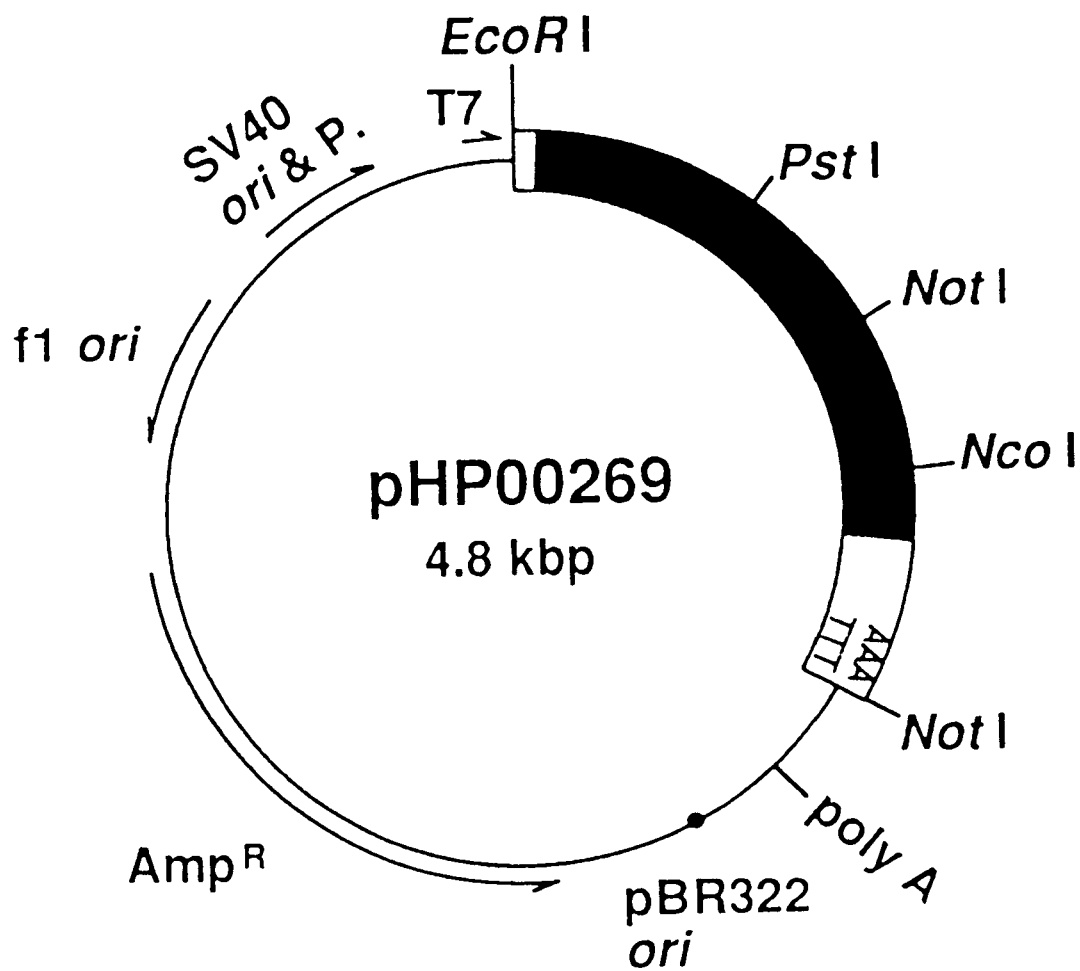
FIG. 1 shows the structure of a cDNA vector of the present invention.

The present invention relates to a human novel cDNA encoding TGF-beta superfamily protein, the protein encoded thereby, and a process for utilizing such proteins or DNA for therapeutic purpose as immunosuppressive agents. The human cDNA of the present invention and the vector containing it can be cloned from a cDNA library prepared using a multifunctional cloning vector. Any vector containing a replication origin derived from a single-stranded phage and a promoter for RNA polymerase upstream of the cDNA cloning site, e.g. pTZ18RP1 or pKA1 (EP-0426455-A2), can be used as a multifunctional cloning vector.

The cDNA of the present invention is synthesized using poly(A)⁺RNA isolated from human cells including tissue cells isolated from human body by a surgical operation and cultured cells of cell lines. For example, poly(A)⁺RNA isolated from human fibrosarcoma cell line HT-1080 can be used. cDNAs can be synthesized according to any method, e.g. the Okayama-Berg method [Okayama, H. & Berg, P., Mol. Cell. Biol. 2: 161–170, 1982] or the Gubler-Hoffman method [Gubler, U. & Hoffman, J., Gene 25: 263–269, 1983]. To obtain full-length cDNAs effectively, the method using a vector primer as described in example is preferable.

Each cDNA is identified by (1) determining the length of the cDNA insert by restriction enzyme digestion, (2) determining an entire sequence of the cDNA, (3) searching a known protein having an amino acid sequence similar to the sequence deduced from the nucleotide sequence of the cDNA, (4) expressing a protein by in vitro translation, (5) expressing the protein in mammalian cells, and (6) assaying a biological activity of the expression product.

Based on the above strategy, the inventors have discovered a human novel cDNA encoding TGF-beta superfamily protein. The obtained cDNA contains an insert of 1.3 kbp including an open reading frame of 927 bp as shown in SEQ ID NO: 5. The open reading frame encodes a protein of 308 amino acid residues (SEQ ID NO:6). The N-terminal region of this protein has a signal sequence which is characteristic of secretory protein and the C-terminal region of 98 amino acid residues shows similarity to the conserved sequence among TGF-beta superfamily proteins.

The TGF-beta superfamily proteins are known to be processed after secretion to produce the C-terminal peptide composed of about 110 to 140 amino acid residues which acts as an active form [Massague, J., Annu. Rev. Cell Biol. 6: 597–641, 1988]. The protein of this invention contains Arg-Arg-Arg sequence at the positions 192 to 194 in the amino acid sequence of SEQ ID NO: 4. At the downstream of this sequence, the protein may be processed to produce an active form which starts from Ala at the position 195, Ala at the position 197, or Asn at the position 199. Thus the active peptide of the present invention contains at least the amino acid sequence described in SEQ ID NO: 2.

The cDNA of the present invention can be readily obtained by screening a human cDNA library prepared from a cell line used in the present invention, using the oligonucleotide probe synthesized based on the nucleotide sequence of the cDNAs of the invention.

It is known that there are many allelic variants in human genes. Thus the present invention includes the DNA variants which contain one or more mutations such as addition, deletion and/or replacement of one or more nucleotides in the nucleotide sequences described in SEQ ID NO: 1 or 3. Thus the present invention includes the proteins which contains one or more mutations such as addition, deletion and/or replacement of one or more amino acids in the amino acid sequence shown in SEQ ID NO: 2 or 4 caused by, for example, above mutations of nucleotides.

The present invention includes any DNA fragments containing the partial nucleotide sequence shown in SEQ ID NO: 1 or 3, and also an antisense strand to said sequence. These DNA fragments can be used as a probe for gene diagnosis.

The present invention further includes DNA or RNA hybridizable under stringent conditions with a nucleotide sequence shown in SEQ ID NO: 1 or 3, and preferably coding for a protein or polypeptide having a property of TGF-beta superfamily protein.

As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which retain substantially the same biological function or activity as the mature polypeptide encoded by the DNA of SEQ ID NO: 1 or 3.

The protein can be produced by isolating from human tissues and cell lines, by synthesizing chemically based on the amino acid sequence of the present invention, and preferably by recombinant techniques using the DNA of the present invention. For example, the protein can be produced in vitro by preparing RNAs via in vitro transcription using the cDNA vectors of the present invention followed by in vitro translation. Furthermore, if the coding region of the cDNA is transferred into other adequate expression vectors, a large amount of the encoded protein can be produced in *E.coli, Bacillus subtilis,* yeast, animal cells and the like.

The protein of the present invention can be produced in bacteria such as *E.coli* by culturing the bacterial cells carrying the expression vector which contains a replication origin, a promoter, a ribosome-binding site, the cDNA, and a terminator. In this case, if the cDNA encoding the mature protein preceded by an initiation codon is inserted into the bacterial expression vector, the mature form can be produced. Alternatively the protein of the present invention can be obtained by processing a fusion protein. The fusion protein with any other protein can be prepared by gene fusion technique and is included in the protein of the present invention.

The protein of the present invention can be secreted in a culture medium as an active form by culturing the mammalian cells carrying an expression vector which contains a replication origin for mammalian cell, a promoter, a splicing site, the cDNA encoding preproprotein, and a poly (A) addition signal.

The present invention includes any peptide fragments containing the partial amino acid sequence described in Sequence ID No. 2 or No. 4. These amino acid fragments can be used as an antigen for preparing polyclonal or monoclonal antibodies. As hereinabove described, the protein is synthesized as a preproform and processed to convert to an active form. Thus, the present invention includes the proteins of all these forms.

The cDNA vector of the present invention can be constructed by transferring the cDNA of this invention into a multifunctional cloning vector carrying an f1 phage origin and an RNA polymerase promoter resided upstream of the cloning site. If the original cDNA library is prepared using the multifunctional cloning vector as described in examples below, the subcloning process can be omitted because the resulting cDNA vectors have already satisfied the requirement.

The proteins of the present invention may be employed as an immunosuppressive agent to treat various autoimmune diseases or in connection with organ transplantations.

The proteins of the present invention may be employed in combination with a suitable pharmaceutical carrier. Such compositions comprise a therapeutically effective amount of the protein, and a pharmaceutically acceptable carrier or excipient. Such a carrier includes saline, buffered saline, dextrose, water, glycerol, ethanol, and combinations thereof. The formulation should suit the mode of administration.

The pharmaceutical compositions may be administered in a convenient manner such as by the oral, topical, intravenous, intraperitoneal, intramuscular, subcutaneous, intravenous or intradermal routes. The amount and dosageregimens of the protein of the present invention administered to a subject will depend on a number of factors such as the mode of administration, the nature of the condition being treated and the judgment of the prescribing physician. Generally they are given in therapeutically effective doses of at least about 10 $\mu$g/kg body weight and in most cases they will be administrated in an amount not in excess of about 8 mg/kg body weight per day.

EXAMPLE

The present invention will now be described by way of examples. The basic procedure of DNA recombination and the reaction conditions were in accordance with the literature [Molecular Cloning. A Laboratory Manual, Cold Spring Harbor Laboratory, 1989]. The restriction enzymes and modified enzymes were purchased from Takara Shuzo except for mentioned otherwise. The buffer compositions and reaction conditions for each enzymatic reaction were as described in the attached protocols.

Preparation of poly(A) RNA

Human fibrosarcoma cell line HT-1080 (ATCC CCL 121) was cultured to a confluent state in a MEM medium containing 10% fetal bovine serum. From these cells, total RNA was prepared using the guanidinium isothiocyanate method [Okayama et al., Method in Enzymology Vol. 164, Academic Press, 1987]. Poly(A)$^+$RNA was purified by oligo-dT cellulose column chromatography as described in the above literature.

Preparation of cDNA library

The multifunctional cloning vector pKA1 (EP-0426455-A2) was digested with KpnI and (dT) tails of about 60 nucleotides were added to both ends using terminal deoxynucleotidyl transferase. After one end of (dT) tails was removed by EcoRV digestion, the resulting vector was used as a vector primer.

The reaction condition of cDNA synthesis was the same as described in the literature [Okayama et al., described above]. Six $\mu$g of poly(A)$^+$RNA was annealed with 2.2 $\mu$g of the vector primer prepared above and then incubated with 144U of reverse transcriptase (Seikagaku Kogyo) at 37° C. for 1. hour to synthesize the first strand cDNA.

After phenol extraction and ethanol precipitation of the reaction mixture, a (dC) tail was added to the first strand cDNA by incubating at 37° C. for 30 min with 2.5M dCTP and 15 units of terminal deoxynucleotidyl transferase. After phenol extraction and ethanol precipitation of the reaction mixture, the product was digested at 55° C. for 2 hours with BstXI (New England Biolabs). After phenol extraction and ethanol precipitation of the reaction mixture, the product was annealed and self-ligated at 12° C. overnight with 300 units of *E.coli* DNA ligase.

After adding dNTP (dATP, dCTP, dGTP, dTTP), 300 units of *E.coli* DNA ligase, 20 units of *E.coli* DNA polymerase I, 15 units of *E.coli* RNase H to the reaction solution, the resulting mixture was incubated at 12° C. for 1 hour and then at 22° C. for 1 hour to replace the RNA strand to a DNA strand. The reaction mixture of above cDNA synthesis was used to transform *E.coli* NM522 (Pharmacia). The transformation was done according to the Hanahan's method [Hanahan, D., J. Mol. Biol. 166: 557–580, 1983].

Cloning and sequencing of cDNA

Part of above cDNA library was spread on a 2× YT agar plate containing 100 μg/ml ampicillin and incubated at 37° C. overnight. Colonies grew on the plate were selected at random, inoculated in 2 ml of a 2× YT medium containing 100 μg/ml ampicillin, and incubated at 37° C. for 2 hours. After infection of helper phage M13KO7, the incubation was continued at 37° C. overnight. The culture medium was centrifuged to separate a cell pellet from a supernatant. A double-stranded plasmid DNA was isolated from the cell pellet by the alkaline lysis method. A single-stranded phage DNA was isolated from the supernatant according to the conventional method.

The double-stranded plasmid DNA was double-digested with EcoRI and NotI, and analyzed on 0.8% agarose gel electrophoresis to determine the size of the cDNA insert. On the other hand, the single-stranded phage DNA was subjected to sequencing reaction and then used for determining the nucleotide sequence with an automated DNA sequencer (Applied Biosystems). The sequencing reaction was carried out using a fluorescent dye-labeled M13 sequencing primer and Taq polymerase (Applied Biosystems kit) in accordance with the reaction conditions described in the protocol attached to the kit.

Identification of cDNA encoding TGF-beta superfamily protein

The clone named HP00269 contained a cDNA insert of 1.3 kbp. Determination of its entire sequence showed that this cDNA contains a 5'-noncoding region of 32 bp, an open reading frame of 927 bp, a 3'-noncoding region of 242 bp, and a poly (A) tail of 40 bp. The open reading frame encodes a protein of 308 amino acid residues (SEQ ID NO:6). Sequence ID No. 5 shows the nucleotide sequence excluding the poly (A) tail of 40 bp. The homology search of protein database revealed that the C terminal 98 amino acid residues of the deduced sequence (HP) shows similarity to the conserved region among TGF-beta superfamily proteins. FIG. 4 shows the result of the alignment. In the table of FIG 4, - represents a gap, . represents the amino acid residues identical to the obtained protein. * under the alignment represents the amino acid residues conserved among all sequences. The percent identity was 35.7% with human BMP-6 (BM, SEQ ID NO:7), 34.7% with GDF-1 (GD, SEQ ID NO:8), 21.4% with inhibin beta (IN, SEQ ID NO:9), and 25.5% with TGF-beta 2 (TG, SEQ ID NO:10). Seven Cys residues were completely conserved. These results suggest that this clone encodes a novel protein belonging to a TGF-beta superfamily.

The N terminal amino acid sequence shows no similarity to any protein registered to the protein database, but has a hydrophobic region which is characteristic of a secretory protein. TGF-beta superfamily protein is known to be converted to an active form composed of the C terminal 110–140 amino acid residues by processing after secretion. The processing occurs at the site preceded by the repeat sequence of basic amino acid residues such as Arg or Lys. The protein of the present invention contains Arg-Arg-Arg at the positions 192 to 194 of the amino acid sequence described by SEQ ID NO: 4, which is a putative processing signal sequence. Thus the protein of the present invention also may be synthesized as prepro-form and the secreted pro-form may be processed with an appropriate protease in the extracellular fluid to be converted to an active mature form containing at least the C terminal 99 amino acid residues described by SEQ ID NO: 2.

The homology search of the DNA database GenBank/EMBL/DDBJ using the obtained nucleotide sequence revealed that two ESTs (accession No. D11716 and D11717) showed 99.3% identity to the region from position 902 to 1200 of the nucleotide sequence described by SEQ ID NO: 5. Since these ESTs have no open reading frame, nobody can expect that these ESTs encode the protein of the present invention.

Expression pattern of the protein in human tissues

Figure 2:
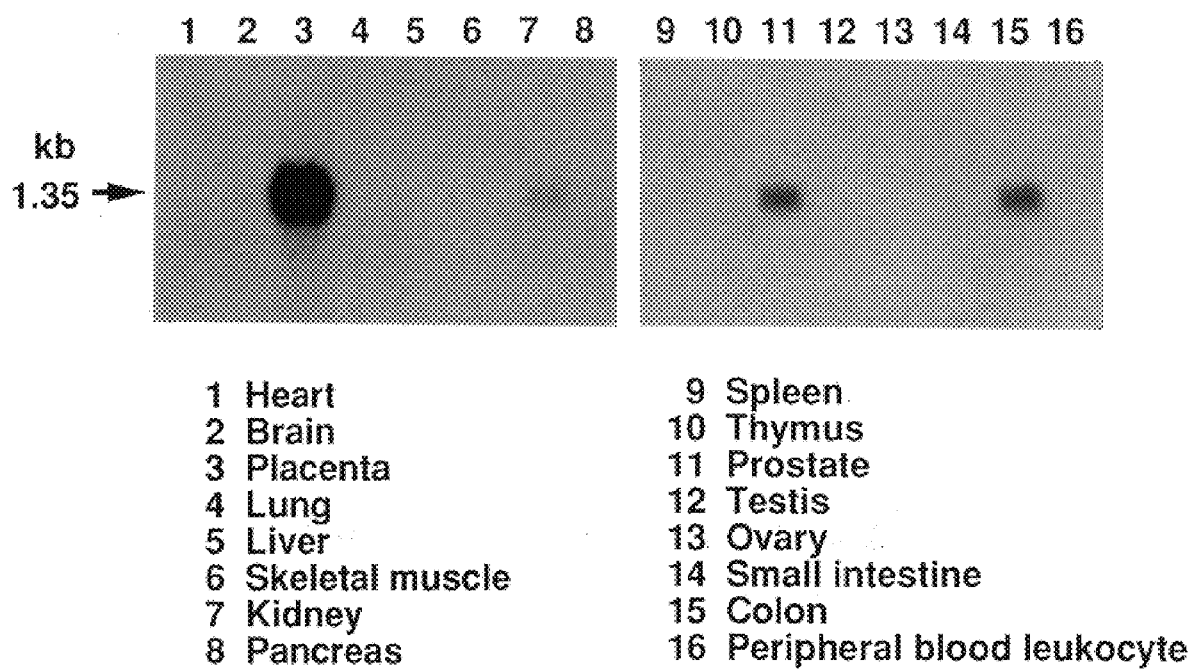
FIG. 2 shows a Northern blot analysis of HP00269.

Northern blot analysis was performed to examine the mRNA level expressed in human tissues. The Northern blots of human tissues purchased from Clontech were used as an mRNA source. A cDNA fragment was labeled with $[\alpha\text{-}^{32}P]$ dCTP (Amersham) using a random primer labeling kit (Takara Shuzo). The hybridization was carried out in the solution attached to the kit according to the manufacturer's protocol. The hybridization signals of the size of about 1.3 kb were found in prostate, colon, kidney, and the especially strong signal in placenta as shown in FIG. 2.

Protein synthesis by in vitro translation

The plasmid pHP00269 was used as a template for in vitro transcription/translation using a kit (Promega). $[^{35}S]$ methionine was added to the reaction solution to obtain a radioisotope-labeled product. The reaction was carried out according to the protocols attached to the kit. The molecular weight of translation product was determined on SDS-polyacrylamide gel electrophoresis followed by autoradiography. The cDNA of the present invention produced the translation product of about 37 kDa, which agreed with the calculated molecular mass of 34,167 in the range of the experimental error.

Expression of an active form in mammalian cells

The monkey kidney-derived cell line COS7 cells were cultured in DMEM medium containing 10% fetal bovine serum at 37° C. in a humidified 5% $CO_2$ incubator. The plasmid pHP00269 of 2 μg was suspended in 1.5 ml of Tris-buffered DMEM medium (T-DMEM, pH 7.5) containing 0.4 mg/ml DEAE-dextran. COS7 cells of $2\times10^5$ were immersed in above suspension and incubated for 4 hours at 37° C. After the medium was removed and DMEM medium containing 10% fetal bovine serum was added, the cells were incubated at 37° C. for 3 days. The cultured medium was used for assays. The pKA1 was transfected into COS7 cells in the same procedure and the culture medium was used as a control.

Enhancement of alkaline phosphatase activity

The culture medium of the transfected cells was added to the 1 ml culture of mouse preosteoblastoma MC3T3-E1 cells which were incubated in alpha MEM medium containing 10% fetal bovine serum. The alkaline phosphatase activity of the cell lysate was determined using a kit (Wako Pure Chemical Industry). Table 2 shows that the expression product of this cDNA can enhance the alkaline phosphatase activity of MC3T3-E1 cells.

TABLE 2

|  | Amount (µl) | Alkaline phosphatase activity (IU/l) |
|---|---|---|
| Sample | 25 | 210 + 10 |
|  | 100 | 280 + 10 |
| Control | 25 | 50 + 2 |
|  | 100 | 60 + 2 |

Immunosuppressive activity

The lymphocyte cells were isolated from spleen of BALB/c mouse and then treated with mitomycin C at 25 mg/ml at 37° C. for 30 min. The treated cells of $1.2 \times 10^6$ were mixed with the lymphocyte cells ($6 \times 10^6$) isolated from spleen of C3H mouse and incubated in 1.6 ml of RPMI-1640 medium containing 10% fetal bovine serum for 5 days. This mixed culture induced the C3H-derived cytotoxic T cell (CTL) which lyses BALB/c cells. The test samples were added into the above culture medium. The C3H lymphocyte cells cultured without adding BALB/c cells were used as a control.

The mixed lymphocyte cells containing CTL (an effector cell, denoted by E) were mixed with target cells (T) which are composed of BALB/c mouse-derived myeloma cell line NS-1/Z cells carrying E.coli beta-galactosidase (beta-gal) gene. The NS-1/Z cells of $10^4$ were mixed with effector cells at an E/T ratio of 5, 10, 20, and incubated in 0.2 ml of RPMI-1640 medium at 37° C. for 4 hours. The activity of beta-galactosidase which was released from lysed target cells into medium were determined and the cytotoxic activity was calculated by the following formula.

Cytotoxic activity (%)=(A–B)×100/(C–B), where A represents beta-gal activity released by cytolysis, B represents beta-gal activity released spontaneously without adding effector cells, and C represents total beta-gal activity of the target cells lysed by 0.0425% Triton-X100.

Figure 3:
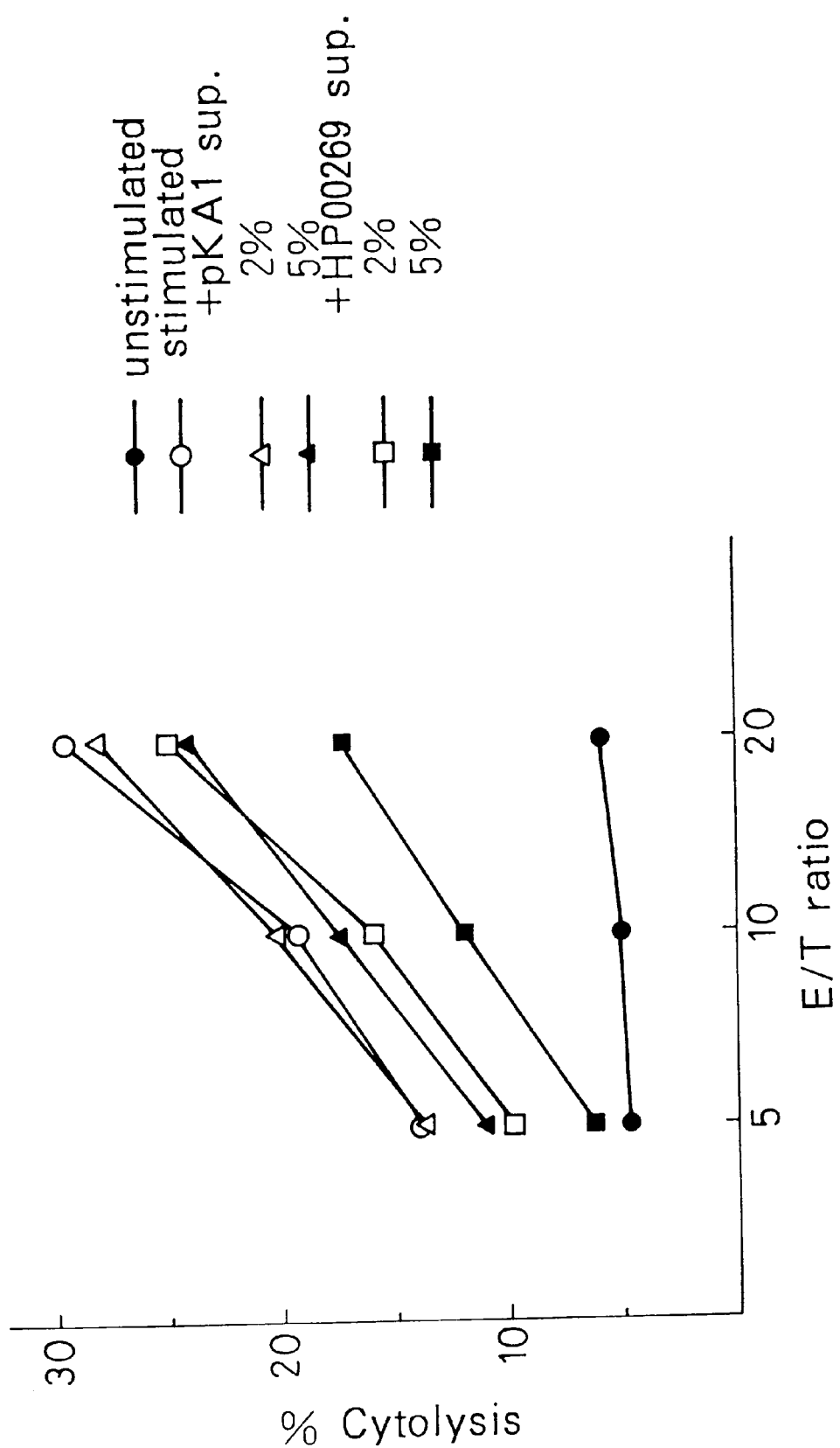
FIG. 3 shows the inhibitory effect of induction of cytotoxic T cell activity by supernatant of COS7 cells carrying the expression vector for HP00269.

As shown in FIG. 3, the supernatant of COS7 cells transfected with pHP00269 inhibited the induction of CTL activity in a dose-dependent manner.

Expression of the protein in E.coli cells

The plasmid pHP00269 was digested with PvuII and then the produced fragment of about 0.5 kbp was isolated from 1% agarose gel. The fragment was subcloned into XmnI-digested pMAL-c2 (New England Biolabs). The ligation mixture was used for transformation of E.coli JM109. The plasmid expressing a fusion protein between maltose-binding protein and the C-terminal region of the protein of the present invention was selected by restriction enzyme mapping and named pMAL269. The transformant carrying the expression plasmid pMAL269 was incubated in 500 ml of LB medium containing 100 µg/ml ampicillin at 37° C. When $A_{600}$ reached at 0.5, isopropylthiogalactoside was added to the concentration of 1 mM. After overnight incubation, the cells were harvested by centrifugation and the pellet was suspended in 25 ml of column buffer containing 10 mM Tris-HCl (pH 7.4), 200 mM NaCl, and 1 mM EDTA. The suspension was lysed by sonication. After centrifugation, the supernatant was applied on 3.5 ml of bed volume of amylose column (New England Biolabs). Bound fusion protein was eluted with 20 ml of column buffer containing 10 mM maltose. The SDS-PAGE analysis showed that the eluted protein has the molecular mass of about 57 kDa which agrees with the calculated value for the fusion protein.

What is claimed is:

1. An isolated protein comprising the amino acid sequence shown in SEQ ID NO:2 or 4.

2. An isolated protein as claimed in claim 1, wherein the sequence of the protein is the amino acid sequence shown in SEQ ID NO: 4.

3. An isolated protein as claimed in claim 1, wherein the amino acid sequence of the protein is the amino acid sequence shown in SEQ ID NO:2.

4. An immunosuppressive composition comprising a protein having the amino acid sequence as shown in SEQ ID NO:2.

5. A method of immunosuppressive therapy, comprising administering to a subject in need of such therapy an immunosuppressive amount of a composition as claimed in claim 4.

6. A method as claimed in claim 5, wherein said subject has an autoimmune disorder.

7. A method as claimed in claim 5, wherein said subject is undergoing organ transplantation.

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 297 base pairs
      (B) TYPE: nucleic acid
      (C) STRANDEDNESS: double
      (D) TOPOLOGY: linear (ix) FEATURE:
      (A) NAME/KEY: CDS
      (B) LOCATION: 1..297

(ix) FEATURE:
      (A) NAME/KEY: mat_peptide
      (B) LOCATION: 1..297

(xi) SEQUENCE DESCRIPTION: SEQ ID NO:1:

```
TGC TGC CGT CTG CAC ACG GTC CGC GCG TCG CTG GAA GAC CTG GGC TGG        48
Cys Cys Arg Leu His Thr Val Arg Ala Ser Leu Glu Asp Leu Gly Trp
  1               5                  10                  15

GCC GAT TGG GTG CTG TCG CCA CGG GAG GTG CAA GTG ACC ATG TGC ATC        96
Ala Asp Trp Val Leu Ser Pro Arg Glu Val Gln Val Thr Met Cys Ile
         20                  25                  30
```

```
GGC GCG TGC CCG AGC CAG TTC CGG GCG GCA AAC ATG CAC GCG CAG ATC      144
Gly Ala Cys Pro Ser Gln Phe Arg Ala Ala Asn Met His Ala Gln Ile
         35                  40                  45

AAG ACG AGC CTG CAC CGC CTG AAG CCC GAC ACG GTG CCA GCG CCC TGC      192
Lys Thr Ser Leu His Arg Leu Lys Pro Asp Thr Val Pro Ala Pro Cys
 50                  55                  60

TGC GTG CCC GCC AGC TAC AAT CCC ATG GTG CTC ATT CAA AAG ACC GAC      240
Cys Val Pro Ala Ser Tyr Asn Pro Met Val Leu Ile Gln Lys Thr Asp
 65                  70                  75                  80

ACC GGG GTG TCG CTC CAG ACC TAT GAT GAC TTG TTA GCC AAA GAC TGC      288
Thr Gly Val Ser Leu Gln Thr Tyr Asp Asp Leu Leu Ala Lys Asp Cys
             85                  90                  95

CAC TGC ATA                                                          297
His Cys Ile
```

(2) INFORMATION FOR SEQ ID NO:2:

(i) SEQUENCE CHARACTERISTICS:
        (A) LENGTH: 99 amino acids
        (B) TYPE: amino acid
        (D) TOPOLOGY: linear (ii) MOLECULE TYPE: protein (xi) SEQUENCE DESCRIPTION: SEQ ID NO:2:

```
Cys Cys Arg Leu His Thr Val Arg Ala Ser Leu Glu Asp Leu Gly Trp
 1               5                  10                  15

Ala Asp Trp Val Leu Ser Pro Arg Glu Val Gln Val Thr Met Cys Ile
             20                  25                  30

Gly Ala Cys Pro Ser Gln Phe Arg Ala Ala Asn Met His Ala Gln Ile
         35                  40                  45

Lys Thr Ser Leu His Arg Leu Lys Pro Asp Thr Val Pro Ala Pro Cys
 50                  55                  60

Cys Val Pro Ala Ser Tyr Asn Pro Met Val Leu Ile Gln Lys Thr Asp
 65                  70                  75                  80

Thr Gly Val Ser Leu Gln Thr Tyr Asp Asp Leu Leu Ala Lys Asp Cys
             85                  90                  95

His Cys Ile
```

(2) INFORMATION FOR SEQ ID NO:3:

(i) SEQUENCE CHARACTERISTICS:
        (A) LENGTH: 924 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..924

(ix) FEATURE:
        (A) NAME/KEY: mat_peptide
        (B) LOCATION: 1..924

(xi) SEQUENCE DESCRIPTION: SEQ ID NO:3:

```
ATG CCC GGG CAA GAA CTC AGG ACG CTG AAT GGC TCT CAG ATG CTC CTG       48
Met Pro Gly Gln Glu Leu Arg Thr Leu Asn Gly Ser Gln Met Leu Leu
 1               5                  10                  15

GTG TTG CTG GTG CTC TCG TGG CTG CCG CAT GGG GGC GCC CTG TCT CTG       96
Val Leu Leu Val Leu Ser Trp Leu Pro His Gly Gly Ala Leu Ser Leu
             20                  25                  30
```

```
GCC GAG GCG AGC CGC GCA AGT TTC CCG GGA CCC TCA GAG TTG CAC ACC        144
Ala Glu Ala Ser Arg Ala Ser Phe Pro Gly Pro Ser Glu Leu His Thr
        35                  40                  45

GAA GAC TCC AGA TTC CGA GAG TTG CGG AAA CGC TAC GAG GAC CTG CTA        192
Glu Asp Ser Arg Phe Arg Glu Leu Arg Lys Arg Tyr Glu Asp Leu Leu
 50                  55                  60

ACC AGG CTG CGG GCC AAC CAG AGC TGG GAA GAT TCG AAC ACC GAC CTC        240
Thr Arg Leu Arg Ala Asn Gln Ser Trp Glu Asp Ser Asn Thr Asp Leu
 65                  70                  75                  80

GTC CCG GCC CCT GCA GTC CGG ATA CTC ACG CCA GAA GTG CGG CTG GGA        288
Val Pro Ala Pro Ala Val Arg Ile Leu Thr Pro Glu Val Arg Leu Gly
                 85                  90                  95

TCC GGC GGC CAC CTG CAC CTG CGT ATC TCT CGG GCC GCC CTT CCC GAG        336
Ser Gly Gly His Leu His Leu Arg Ile Ser Arg Ala Ala Leu Pro Glu
            100                 105                 110

GGG CTC CCC GAG GCC TCC CGC CTT CAC CGG GCT CTG TTC CGG CTG TCC        384
Gly Leu Pro Glu Ala Ser Arg Leu His Arg Ala Leu Phe Arg Leu Ser
        115                 120                 125

CCG ACG GCG TCA AGG TCG TGG GAC GTG ACA CGA CCT CTG CGG CGT CAG        432
Pro Thr Ala Ser Arg Ser Trp Asp Val Thr Arg Pro Leu Arg Arg Gln
130                 135                 140

CTC AGC CTT GCA AGA CCC CAG GCG CCC GCG CTG CAC CTG CGA CTG TCG        480
Leu Ser Leu Ala Arg Pro Gln Ala Pro Ala Leu His Leu Arg Leu Ser
145                 150                 155                 160

CCG CCG CCG TCG CAG TCG GAC CAA CTG CTG GCA GAA TCT TCG TCC GCA        528
Pro Pro Pro Ser Gln Ser Asp Gln Leu Leu Ala Glu Ser Ser Ser Ala
                165                 170                 175

CGG CCC CAG CTG GAG TTG CAC TTG CGG CCG CAA GCC GCC AGG GGG CGC        576
Arg Pro Gln Leu Glu Leu His Leu Arg Pro Gln Ala Ala Arg Gly Arg
            180                 185                 190

CGC AGA GCG CGT GCG CGC AAC GGG GAC CAC TGT CCG CTC GGG CCC GGG        624
Arg Arg Ala Arg Ala Arg Asn Gly Asp His Cys Pro Leu Gly Pro Gly
        195                 200                 205

CGT TGC TGC CGT CTG CAC ACG GTC CGC GCG TCG CTG GAA GAC CTG GGC        672
Arg Cys Cys Arg Leu His Thr Val Arg Ala Ser Leu Glu Asp Leu Gly
210                 215                 220

TGG GCC GAT TGG GTG CTG TCG CCA CGG GAG GTG CAA GTG ACC ATG TGC        720
Trp Ala Asp Trp Val Leu Ser Pro Arg Glu Val Gln Val Thr Met Cys
225                 230                 235                 240

ATC GGC GCG TGC CCG AGC CAG TTC CGG GCG GCA AAC ATG CAC GCG CAG        768
Ile Gly Ala Cys Pro Ser Gln Phe Arg Ala Ala Asn Met His Ala Gln
                245                 250                 255

ATC AAG ACG AGC CTG CAC CGC CTG AAG CCC GAC ACG GTG CCA GCG CCC        816
Ile Lys Thr Ser Leu His Arg Leu Lys Pro Asp Thr Val Pro Ala Pro
            260                 265                 270

TGC TGC GTG CCC GCC AGC TAC AAT CCC ATG GTG CTC ATT CAA AAG ACC        864
Cys Cys Val Pro Ala Ser Tyr Asn Pro Met Val Leu Ile Gln Lys Thr
        275                 280                 285

GAC ACC GGG GTG TCG CTC CAG ACC TAT GAT GAC TTG TTA GCC AAA GAC        912
Asp Thr Gly Val Ser Leu Gln Thr Tyr Asp Asp Leu Leu Ala Lys Asp
290                 295                 300

TGC CAC TGC ATA                                                        924
Cys His Cys Ile
305

(2) INFORMATION FOR SEQ ID NO:4:

(i) SEQUENCE CHARACTERISTICS:
          (A) LENGTH: 308 amino acids
          (B) TYPE: amino acid
          (D) TOPOLOGY: linear
```

(ii) MOLECULE TYPE: protein (xi) SEQUENCE DESCRIPTION: SEQ ID NO:4:

Met Pro Gly Gln Glu Leu Arg Thr Leu Asn Gly Ser Gln Met Leu Leu
 1               5                  10                  15

Val Leu Leu Val Leu Ser Trp Leu Pro His Gly Gly Ala Leu Ser Leu
            20                  25                  30

Ala Glu Ala Ser Arg Ala Ser Phe Pro Gly Pro Ser Glu Leu His Thr
        35                  40                  45

Glu Asp Ser Arg Phe Arg Glu Leu Arg Lys Arg Tyr Glu Asp Leu Leu
    50                  55                  60

Thr Arg Leu Arg Ala Asn Gln Ser Trp Glu Asp Ser Asn Thr Asp Leu
65                  70                  75                  80

Val Pro Ala Pro Ala Val Arg Ile Leu Thr Pro Glu Val Arg Leu Gly
                85                  90                  95

Ser Gly Gly His Leu His Leu Arg Ile Ser Arg Ala Ala Leu Pro Glu
            100                 105                 110

Gly Leu Pro Glu Ala Ser Arg Leu His Arg Ala Leu Phe Arg Leu Ser
        115                 120                 125

Pro Thr Ala Ser Arg Ser Trp Asp Val Thr Arg Pro Leu Arg Arg Gln
    130                 135                 140

Leu Ser Leu Ala Arg Pro Gln Ala Pro Ala Leu His Leu Arg Leu Ser
145                 150                 155                 160

Pro Pro Pro Ser Gln Ser Asp Gln Leu Leu Ala Glu Ser Ser Ser Ala
                165                 170                 175

Arg Pro Gln Leu Glu Leu His Leu Arg Pro Gln Ala Ala Arg Gly Arg
            180                 185                 190

Arg Arg Ala Arg Ala Arg Asn Gly Asp His Cys Pro Leu Gly Pro Gly
        195                 200                 205

Arg Cys Cys Arg Leu His Thr Val Arg Ala Ser Leu Glu Asp Leu Gly
    210                 215                 220

Trp Ala Asp Trp Val Leu Ser Pro Arg Glu Val Gln Val Thr Met Cys
225                 230                 235                 240

Ile Gly Ala Cys Pro Ser Gln Phe Arg Ala Ala Asn Met His Ala Gln
                245                 250                 255

Ile Lys Thr Ser Leu His Arg Leu Lys Pro Asp Thr Val Pro Ala Pro
            260                 265                 270

Cys Cys Val Pro Ala Ser Tyr Asn Pro Met Val Leu Ile Gln Lys Thr
        275                 280                 285

Asp Thr Gly Val Ser Leu Gln Thr Tyr Asp Asp Leu Leu Ala Lys Asp
    290                 295                 300

Cys His Cys Ile
305

(2) INFORMATION FOR SEQ ID NO:5:

(i) SEQUENCE CHARACTERISTICS:
      (A) LENGTH: 1201 base pairs
      (B) TYPE: nucleic acid
      (C) STRANDEDNESS: double
      (D) TOPOLOGY: linear (ix) FEATURE:
      (A) NAME/KEY: CDS
      (B) LOCATION: 33..956

(ix) FEATURE:

-continued (A) NAME/KEY: mat_peptide
(B) LOCATION: 33..956

(xi) SEQUENCE DESCRIPTION: SEQ ID NO:5:

```
AGTCCCAGCT CAGAGCCGCA ACCTGCACAG CC ATG CCC GGG CAA GAA CTC AGG        53
                                    Met Pro Gly Gln Glu Leu Arg
                                      1               5

ACG CTG AAT GGC TCT CAG ATG CTC CTG GTG TTG CTG GTG CTC TCG TGG       101
Thr Leu Asn Gly Ser Gln Met Leu Leu Val Leu Leu Val Leu Ser Trp
         10                  15                  20

CTG CCG CAT GGG GGC GCC CTG TCT CTG GCC GAG GCG AGC CGC GCA AGT       149
Leu Pro His Gly Gly Ala Leu Ser Leu Ala Glu Ala Ser Arg Ala Ser
 25                  30                  35

TTC CCG GGA CCC TCA GAG TTG CAC ACC GAA GAC TCC AGA TTC CGA GAG       197
Phe Pro Gly Pro Ser Glu Leu His Thr Glu Asp Ser Arg Phe Arg Glu
 40                  45                  50                  55

TTG CGG AAA CGC TAC GAG GAC CTG CTA ACC AGG CTG CGG GCC AAC CAG       245
Leu Arg Lys Arg Tyr Glu Asp Leu Leu Thr Arg Leu Arg Ala Asn Gln
             60                  65                  70

AGC TGG GAA GAT TCG AAC ACC GAC CTC GTC CCG GCC CCT GCA GTC CGG       293
Ser Trp Glu Asp Ser Asn Thr Asp Leu Val Pro Ala Pro Ala Val Arg
                 75                  80                  85

ATA CTC ACG CCA GAA GTG CGG CTG GGA TCC GGC GGC CAC CTG CAC CTG       341
Ile Leu Thr Pro Glu Val Arg Leu Gly Ser Gly Gly His Leu His Leu
             90                  95                 100

CGT ATC TCT CGG GCC GCC CTT CCC GAG GGG CTC CCC GAG GCC TCC CGC       389
Arg Ile Ser Arg Ala Ala Leu Pro Glu Gly Leu Pro Glu Ala Ser Arg
        105                 110                 115

CTT CAC CGG GCT CTG TTC CGG CTG TCC CCG ACG GCG TCA AGG TCG TGG       437
Leu His Arg Ala Leu Phe Arg Leu Ser Pro Thr Ala Ser Arg Ser Trp
120                 125                 130                 135

GAC GTG ACA CGA CCT CTG CGG CGT CAG CTC AGC CTT GCA AGA CCC CAG       485
Asp Val Thr Arg Pro Leu Arg Arg Gln Leu Ser Leu Ala Arg Pro Gln
                140                 145                 150

GCG CCC GCG CTG CAC CTG CGA CTG TCG CCG CCG CCG TCG CAG TCG GAC       533
Ala Pro Ala Leu His Leu Arg Leu Ser Pro Pro Pro Ser Gln Ser Asp
            155                 160                 165

CAA CTG CTG GCA GAA TCT TCG TCC GCA CGG CCC CAG CTG GAG TTG CAC       581
Gln Leu Leu Ala Glu Ser Ser Ser Ala Arg Pro Gln Leu Glu Leu His
        170                 175                 180

TTG CGG CCG CAA GCC GCC AGG GGG CGC CGC AGA GCG CGT GCG CGC AAC       629
Leu Arg Pro Gln Ala Ala Arg Gly Arg Arg Arg Ala Arg Ala Arg Asn
185                 190                 195

GGG GAC CAC TGT CCG CTC GGG CCC GGG CGT TGC TGC CGT CTG CAC ACG       677
Gly Asp His Cys Pro Leu Gly Pro Gly Arg Cys Cys Arg Leu His Thr
200                 205                 210                 215

GTC CGC GCG TCG CTG GAA GAC CTG GGC TGG GCC GAT TGG GTG CTG TCG       725
Val Arg Ala Ser Leu Glu Asp Leu Gly Trp Ala Asp Trp Val Leu Ser
                220                 225                 230

CCA CGG GAG GTG CAA GTG ACC ATG TGC ATC GGC GCG TGC CCG AGC CAG       773
Pro Arg Glu Val Gln Val Thr Met Cys Ile Gly Ala Cys Pro Ser Gln
            235                 240                 245

TTC CGG GCG GCA AAC ATG CAC GCG CAG ATC AAG ACG AGC CTG CAC CGC       821
Phe Arg Ala Ala Asn Met His Ala Gln Ile Lys Thr Ser Leu His Arg
        250                 255                 260

CTG AAG CCC GAC ACG GTG CCA GCG CCC TGC TGC GTG CCC GCC AGC TAC       869
Leu Lys Pro Asp Thr Val Pro Ala Pro Cys Cys Val Pro Ala Ser Tyr
265                 270                 275

AAT CCC ATG GTG CTC ATT CAA AAG ACC GAC ACC GGG GTG TCG CTC CAG       917
Asn Pro Met Val Leu Ile Gln Lys Thr Asp Thr Gly Val Ser Leu Gln
```

-continued

```
          280                 285                 290                 295
ACC TAT GAT GAC TTG TTA GCC AAA GAC TGC CAC TGC ATA TGAGCAGTCC              966
Thr Tyr Asp Asp Leu Leu Ala Lys Asp Cys His Cys Ile
                        300                 305

TGGTCCTTCC ACTGTGCACC TGCGCGGGGG AGGCGACCTC AGTTGTCCTG CCCTGTGGAA          1026

TGGGCTCAAG GTTCCTGAGA CACCCGATTC CTGCCCAAAC AGCTGTATTT ATATAAGTCT          1086

GTTATTTATT ATTAATTTAT TGGGGTGACC TTCTTGGGGA CTCGGGGGCT GGTCTGATGG          1146

AACTGTGTAT TTATTTAAAA CTCTGGTGAT AAAAATAAAG CTGTCTGAAC TGTTC              1201
```

(2) INFORMATION FOR SEQ ID NO:6:

(i) SEQUENCE CHARACTERISTICS:
        (A) LENGTH: 308 amino acids
        (B) TYPE: amino acid
        (D) TOPOLOGY: linear (ii) MOLECULE TYPE: protein (xi) SEQUENCE DESCRIPTION: SEQ ID NO:6:

```
Met Pro Gly Gln Glu Leu Arg Thr Leu Asn Gly Ser Gln Met Leu Leu
 1               5                  10                  15

Val Leu Val Leu Ser Trp Leu Pro His Gly Gly Ala Leu Ser Leu
            20                  25                  30

Ala Glu Ala Ser Arg Ala Ser Phe Pro Gly Pro Ser Glu Leu His Thr
            35                  40                  45

Glu Asp Ser Arg Phe Arg Glu Leu Arg Lys Arg Tyr Glu Asp Leu Leu
        50                  55                  60

Thr Arg Leu Arg Ala Asn Gln Ser Trp Glu Asp Ser Asn Thr Asp Leu
65                  70                  75                  80

Val Pro Ala Pro Ala Val Arg Ile Leu Thr Pro Glu Val Arg Leu Gly
            85                  90                  95

Ser Gly Gly His Leu His Leu Arg Ile Ser Arg Ala Ala Leu Pro Glu
            100                 105                 110

Gly Leu Pro Glu Ala Ser Arg Leu His Arg Ala Leu Phe Arg Leu Ser
            115                 120                 125

Pro Thr Ala Ser Arg Ser Trp Asp Val Thr Arg Pro Leu Arg Arg Gln
        130                 135                 140

Leu Ser Leu Ala Arg Pro Gln Ala Pro Ala Leu His Leu Arg Leu Ser
145                 150                 155                 160

Pro Pro Pro Ser Gln Ser Asp Gln Leu Leu Ala Glu Ser Ser Ser Ala
                165                 170                 175

Arg Pro Gln Leu Glu Leu His Leu Arg Pro Gln Ala Ala Arg Gly Arg
            180                 185                 190

Arg Arg Ala Arg Ala Arg Asn Gly Asp His Cys Pro Leu Gly Pro Gly
        195                 200                 205

Arg Cys Cys Arg Leu His Thr Val Arg Ala Ser Leu Glu Asp Leu Gly
    210                 215                 220

Trp Ala Asp Trp Val Leu Ser Pro Arg Glu Val Gln Val Thr Met Cys
225                 230                 235                 240

Ile Gly Ala Cys Pro Ser Gln Phe Arg Ala Ala Asn Met His Ala Gln
                245                 250                 255

Ile Lys Thr Ser Leu His Arg Leu Lys Pro Asp Thr Val Pro Ala Pro
            260                 265                 270

Cys Cys Val Pro Ala Ser Tyr Asn Pro Met Val Leu Ile Gln Lys Thr
    275                 280                 285
```

```
Asp Thr Gly Val Ser Leu Gln Thr Tyr Asp Asp Leu Leu Ala Lys Asp
    290                 295                 300

Cys His Cys Ile
305
```

(2) INFORMATION FOR SEQ ID NO:7:

(i) SEQUENCE CHARACTERISTICS:
        (A) LENGTH: 103 amino acids
        (B) TYPE: amino acid
        (C) STRANDEDNESS: single
        (D) TOPOLOGY: linear (xi) SEQUENCE DESCRIPTION: SEQ ID NO:7:

```
Cys Arg Lys His Glu Leu Tyr Val Ser Phe Gln Glu Asp Leu Gly Trp
1               5                   10                  15

Gln Asp Trp Ile Ile Ala Pro Lys Gly Tyr Ala Ala Asn Tyr Cys Asp
                20                  25                  30

Gly Glu Cys Ser Phe Pro Leu Asn Ala His Met Asn Ala Thr Asn His
            35                  40                  45

Ala Ile Val Gln Thr Leu Val His Leu Met Asn Pro Glu Tyr Val Pro
    50                  55                  60

Lys Pro Cys Cys Ala Pro Thr Lys Leu Asn Ala Ile Ser Val Leu Tyr
65                  70                  75                  80

Phe Asp Asp Asn Ser Asn Val Ile Leu Lys Lys Tyr Arg Asn Met Val
                85                  90                  95

Val Arg Ala Cys Gly Cys His
            100
```

(2) INFORMATION FOR SEQ ID NO:8:

(i) SEQUENCE CHARACTERISTICS:
        (A) LENGTH: 106 amino acids
        (B) TYPE: amino acid
        (C) STRANDEDNESS: single
        (D) TOPOLOGY: linear (xi) SEQUENCE DESCRIPTION: SEQ ID NO:8:

```
Cys Arg Ala Arg Arg Leu Tyr Val Ser Phe Arg Glu Val Gly Trp His
1               5                   10                  15

Arg Trp Val Ile Ala Pro Arg Gly Phe Leu Ala Asn Tyr Cys Gln Gly
                20                  25                  30

Gln Cys Ala Leu Pro Val Ala Leu Ser Gly Ser Gly Gly Pro Pro Ala
            35                  40                  45

Leu Asn His Ala Val Leu Arg Ala Leu Met His Ala Ala Ala Pro Gly
    50                  55                  60

Ala Ala Asp Leu Pro Cys Cys Val Pro Ala Arg Leu Ser Pro Ile Ser
65                  70                  75                  80

Val Leu Phe Phe Asp Asn Ser Asp Asn Val Val Leu Arg Gln Tyr Glu
                85                  90                  95

Asp Met Val Val Asp Glu Cys Gly Cys Arg
            100                 105
```

(2) INFORMATION FOR SEQ ID NO:9:

(i) SEQUENCE CHARACTERISTICS:
        (A) LENGTH: 104 amino acids
        (B) TYPE: amino acid
        (C) STRANDEDNESS: single
        (D) TOPOLOGY: linear -continued (xi) SEQUENCE DESCRIPTION: SEQ ID NO:9:

```
Cys Arg Gln Gln Phe Phe Ile Asp Phe Arg Leu Ile Gly Trp Asn Asp
1               5                   10                  15

Trp Ile Ile Ala Pro Thr Gly Tyr Tyr Gly Asn Tyr Cys Glu Gly Ser
            20                  25                  30

Cys Pro Ala Tyr Leu Ala Gly Val Pro Gly Ser Ala Ser Ser Phe His
            35                  40                  45

Thr Ala Val Val Asn Gln Tyr Arg Met Arg Gly Leu Asn Pro Gly Thr
            50                  55                  60

Val Asn Ser Cys Cys Ile Pro Thr Lys Leu Ser Thr Met Ser Met Leu
65              70                  75                  80

Tyr Phe Asp Asp Glu Tyr Asn Ile Val Lys Arg Asp Val Pro Asn Met
                85                  90                  95

Ile Val Glu Glu Cys Gly Cys Ala
                100
```

(2) INFORMATION FOR SEQ ID NO:10:

(i) SEQUENCE CHARACTERISTICS:
        (A) LENGTH: 97 amino acids
        (B) TYPE: amino acid
        (C) STRANDEDNESS: single
        (D) TOPOLOGY: linear (xi) SEQUENCE DESCRIPTION: SEQ ID NO:10:

```
Cys Leu Arg Pro Leu Tyr Ile Asp Phe Lys Arg Asp Leu Gly Trp Lys
1               5                   10                  15

Trp Ile His Glu Pro Lys Gly Tyr Asn Ala Asn Phe Cys Ala Gly Ala
            20                  25                  30

Cys Pro Tyr Leu Trp Ser Ser Asp Thr Gln His Ser Arg Val Leu Ser
            35                  40                  45

Leu Tyr Asn Thr Ile Asn Pro Glu Ala Ser Ala Ser Pro Cys Cys Val
        50                  55                  60

Ser Gln Asp Leu Glu Pro Leu Thr Ile Leu Tyr Tyr Ile Gly Lys Thr
65              70                  75                  80

Pro Lys Ile Glu Gln Leu Ser Asn Met Ile Val Lys Ser Cys Lys Cys
                85                  90                  95

Ser
```